United States Patent [19]

Nottke

[11] Patent Number: 4,917,100
[45] Date of Patent: Apr. 17, 1990

[54] BIOPSY NEEDLE FOR USE WITH SPRING-OPERATED ACTUATING MECHANISM

[76] Inventor: James E. Nottke, 8609 Piper La., Largo, Fla. 34647

[21] Appl. No.: 348,871

[22] Filed: May 8, 1989

[51] Int. Cl.$^4$ .............................................. A61B 10/00
[52] U.S. Cl. .................................... 128/749; 128/754; 606/167; 606/171
[58] Field of Search ............... 128/749, 751, 752, 753, 128/754, 755; 606/159, 166, 167, 170, 171, 184, 185

[56] References Cited

U.S. PATENT DOCUMENTS

| | | | |
|---|---|---|---|
| 2,705,949 | 4/1955 | Silverman | 128/2 |
| 3,477,423 | 11/1969 | Griffith | 128/2 |
| 4,600,014 | 7/1986 | Beraha | 128/754 |
| 4,776,346 | 10/1988 | Beraha et al. | 128/754 |

Primary Examiner—Max Hindenburg
Assistant Examiner—Randy Shay

[57] ABSTRACT

A biopsy needles for use with a spring-operated actuating mechanism. The biopsy needle has a slide attached to the proximal end of its cannula and having an elongated slot extending longitudinally away from the cannula and a laterally projecting segment at the end away from the cannula. The biopsy needle also has a slide attached to the proximal end of its obturator and having a laterally projecting outer segment that extends on the opposite side from the laterally projecting segment of the cannula slide. The laterally projecting segment of the obturator slide is offset from the laterally projecting segment of the cannula slide in the direction toward the cannula and obturator when the obturator slide is at the end of the slot in the cannula slide away from the cannula and the obturator.

5 Claims, 2 Drawing Sheets

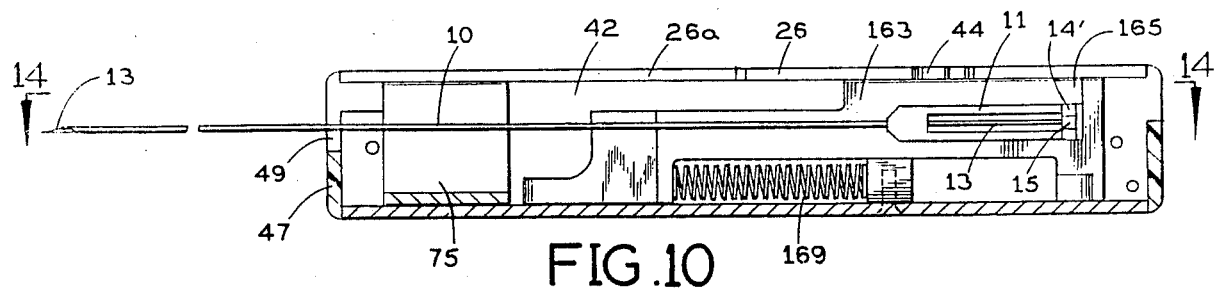
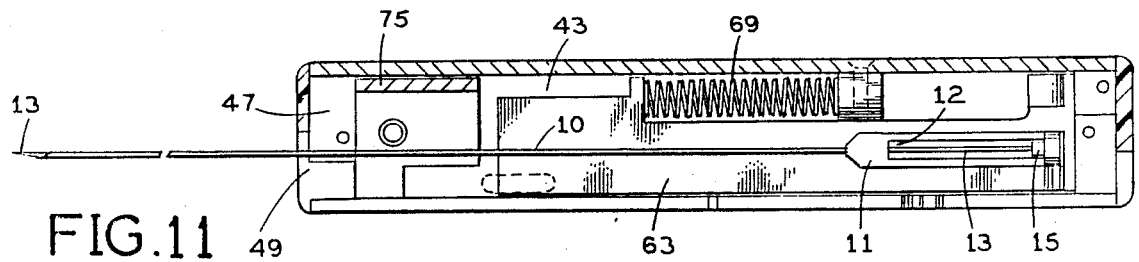
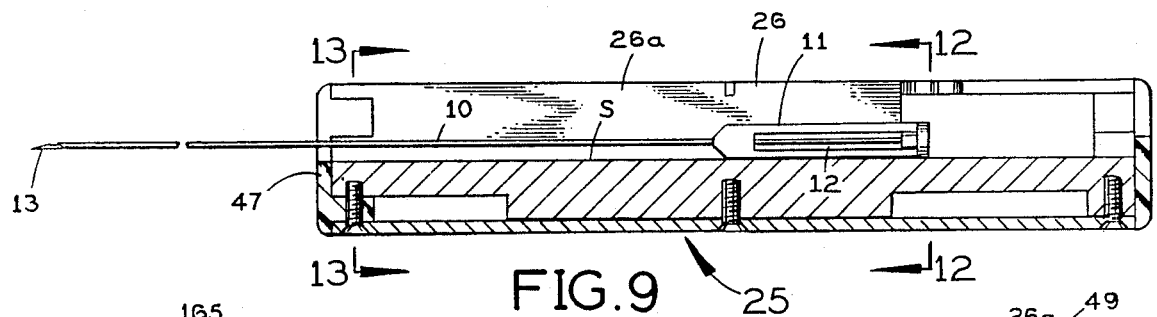
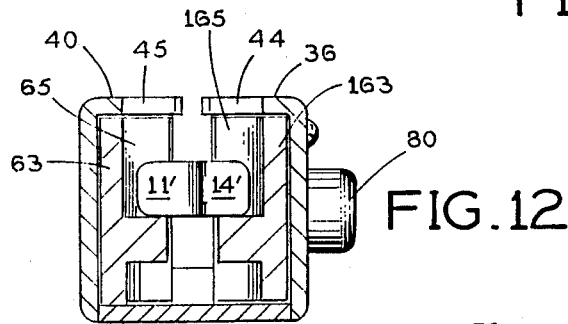
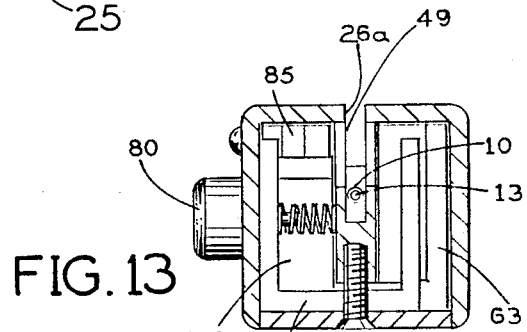
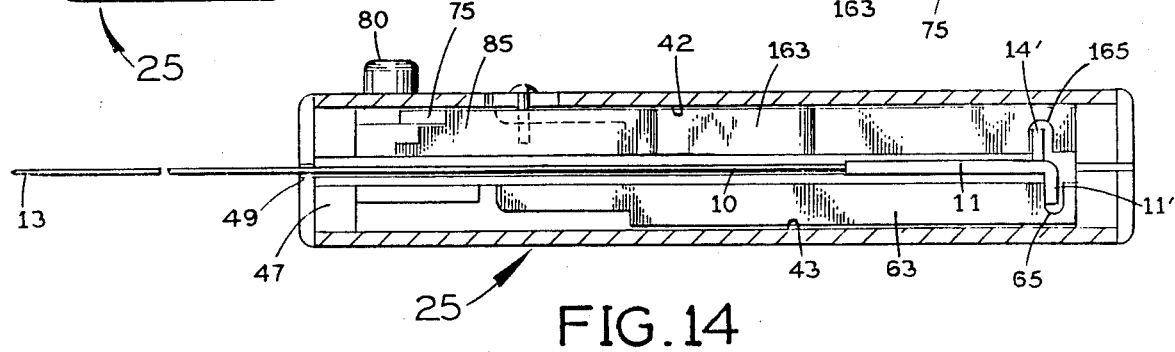

4,917,100

BIOPSY NEEDLE FOR USE WITH SPRING-OPERATED ACTUATING MECHANISM

CROSS-REFERENCE TO RELATED APPLICATION

My copending U.S. patent application Ser. No. 268,729, filed Nov. 7, 1988, discloses and claims a spring-operated actuating mechanism for a biopsy needle. The present invention relates to a novel biopsy needle for use with such an actuating mechanism modified dimensionally but without significant change in how its moving parts operate.

SUMMARY OF THE INVENTION

This invention relates to a novel biopsy needle unit which is particularly adapted for use with a spring-powered actuating mechanism that operates essentially as disclosed and claimed in my U.S. patent application Ser. No. 268,729, filed Nov. 7, 1988.

A principal object of this invention is to provide a novel biopsy needle which enables a reduction in the width of the actuating mechanism which operates it, thereby making it more convenient for a surgeon to use the combined actuating mechanism and biopsy needle.

Another object of this invention is to provide such a biopsy needle which can be inserted in the actuating mechanism only one way, thereby insuring that the actuating mechanism will operate the biopsy needle correctly.

In accordance with the present invention, the biopsy needle has a slide affixed to the proximal end of its cannula and a slide affixed to the proximal end of its obturator or stylet. The cannula slide has an elongated slot extending away from the cannula and longitudinally aligned with it, and a laterally projecting segment at its end away from the cannula. The obturator slide has an inner segment slidably received in the slot in the cannula slide and an outer segment which projects laterally on the opposite side from the laterally projecting segment of the cannula slide. When the obturator slide is at the end of the slot away from the cannula, its laterally projecting outer segment is offset longitudinally from the laterally projecting segment of the cannula slide in the direction of the cannula and the obturator. This is the retracted position of the obturator with respect to the cannula, in which the usual specimen-receiving recess in the obturator is covered by the cannula. When the obturator slide is slid to the opposite end of the slot in the cannula slide, the specimen-receiving recess in the cannula becomes exposed beyond the distal end of the cannula.

Further objects and advantages of this invention will be apparent from the following detailed description of a presently preferred embodiment which is illustrated schematically in the accompanying drawings.

DESCRIPTION OF THE DRAWINGS

FIG. 9 is a longitudinal section taken along the line 9—9 in FIG. 1;

FIG. 10 is a longitudinal section taken along the line 10—10 in FIG. 1, with the biopsy needle retracted to the phantom line position in FIG. 1 and looking at the obturator slide bar in the actuating mechanism for the biopsy needle;

FIG. 11 is a longitudinal section taken along the line 11—11 in FIG. 1, with the biopsy needle retracted to the phantom line position in FIG. 1 and looking at the cannula slide bar in the actuating mechanism;

FIG. 12 is a cross-section taken along the line 12—12 in FIG. 9 behind the cannula slide;

FIG. 13 is a cross-section taken along the line 13—13 in FIG. 9 through the front piece 47 of the housing of the actuating mechanism; and FIG. 14 is a longitudinal section taken along the line 14—14 in FIG. 10.

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

DETAILED DESCRIPTION

Figures 2, 3:
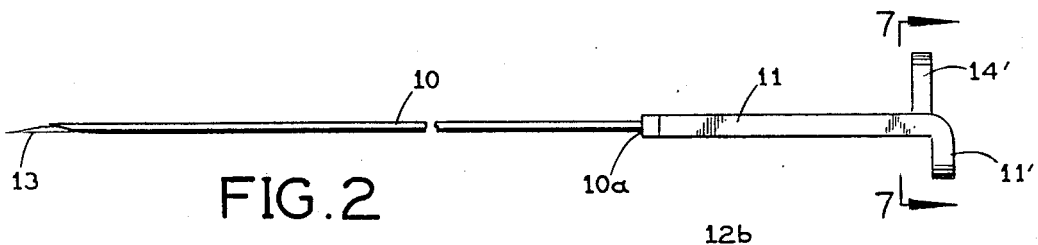
FIG. 2 is a side elevation of this biopsy needle with its obturator or stylet retracted into its cannula.
FIG. 3 is a top plan view of the biopsy needle in this retracted position of its obturator.
Figures 4, 5:
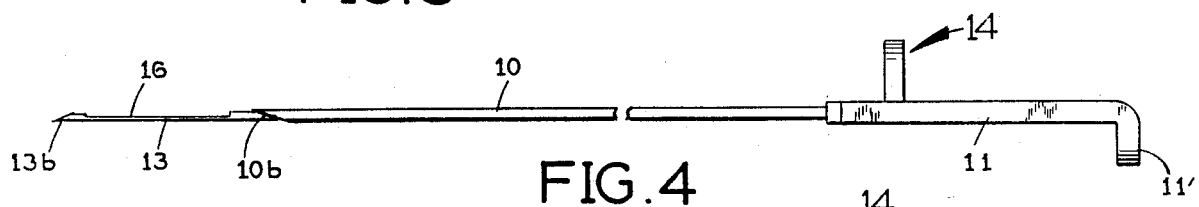
FIG. 4 is a side elevation of the biopsy needle with its obturator extended beyond the distal end of the cannula to expose its specimen-receiving recess.
FIG. 5 is a top elevation of the biopsy needle in the FIG. 4 position.
Figure 6:
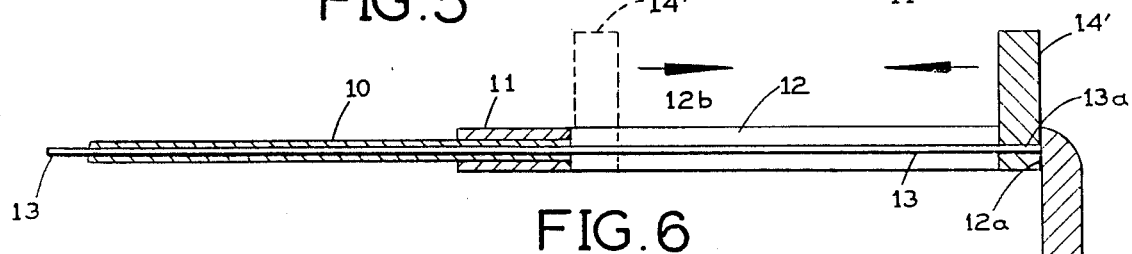
FIG. 6 is a longitudinal vertical section taken along the line 6—6 in FIG. 3.

Referring to FIGS. 2 and 3, one integral part of the present biopsy needle consists of an elongated cylindrical cannula 10 and a cannula slide 11 rigidly attached to the cannula at the latter's proximal end 10a. The cannula slide for almost its entire length is a longitudinal extension of the cannula. As shown in FIGS. 3, 5 and 6, the cannula slide has a slot 12 that is elongated longitudinally of the cannula slide and is open through the complete thickness of that slide from side to side. Slot 12 is a widened longitudinal extension of the longitudinal passage through the cannula. This slot is closed at its back end 12a and at its front end at 12b except where it opens into the cannula passageway. Immediately behind the back end of its slot 12, the cannula slide terminates in a laterally projecting segment 11', which extends perpendicular to the conjoint longitudinal axis of the cannula slide and the cannula on one side of that axis.

Figures 7, 8:
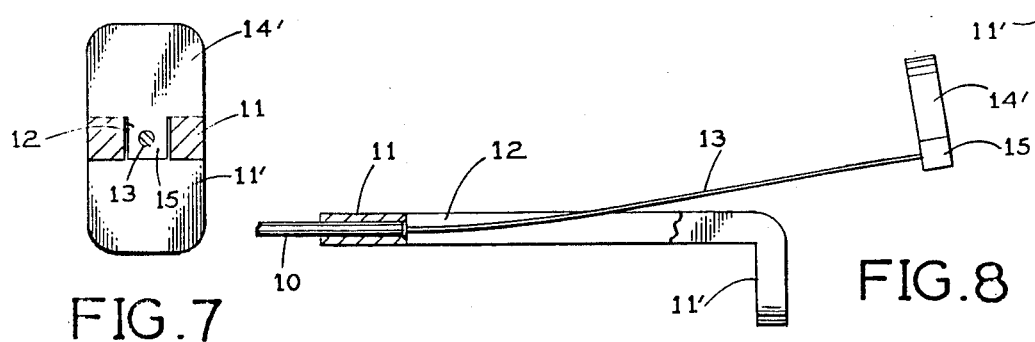
FIG. 7 is a cross-section taken along the line 7—7 in FIG. 2.
FIG. 8 is a view similar to FIG. 6 and showing the obturator being slidably inserted into or removed from the cannula.

The other integral part of the present biopsy needle consists of an elongated obturator or stylet 13 (FIGS. 4, 5 and 6) and an obturator slide 14 rigidly attached to the obturator at the latter's proximal end 13a. The obturator is slidably received in the longitudinal passage through the cannula. As shown in FIG. 7, the obturator slide 14 is generally T-shaped in cross-section, with a rectangular bottom segment 15 that is slidably received in slot 12 in obturator slide 11 and a wider top segment 14' that extends slidably across the top of the cannula slide on opposite sides of the its longitudinal slot 12. The top segment 14' is a laterally projecting segment of the obturator slide which extends perpendicular to the conjoint longitudinal axis of the cannula slide 11 and the cannula 10 on the opposite side of that axis from the laterally projecting segment 11' of the cannula slide.

As shown in FIG. 6, the obturator slide 14 is slidably adjustable along the slot 12 in the cannula slide between a first position (shown in full lines), in which the bottom segment 15 of the obturator slide abuts against the back end 12a of slot 12 and the laterally projecting segment 14' of the obturator slide is slightly offset in front of the oppositely projecting transverse segment 11' of the cannula slide, and a second position (shown in phantom), in which the bottom segment 15 of the obturator slide 14 engages the front end 12b of slot 12 in cannula slide 11. As shown in FIGS. 2 and 3, in the just-specified first position of the obturator slide 14 with respect to the cannula slide 11, the cannula 10 covers the obturator 13 forward beyond the cannula slide except the distal end tip of the obdurator. This first position is the retracted position of the obturator and obturator slide with respect to the cannula and cannula slide. As shown in FIGS. 4 and 5, in the above-specified second position of the obturator slide 14 along the cannula slide 11, the obturator 13 at its distal end 13b extends beyond the distal end 10b of cannula 10, exposing the usual specimen-receiving recess 16 which is located near the distal end 13b of the obturator. This second position is the extended position of the obturator and obturator slide with respect to the cannula and cannula slide.

As shown in FIG. 8, the obturator 13 is flexible enough to permit its slidable removal from or insertion into the cannula 10 at the front end 12b of slot 12 in the cannula slide 11. For insertion, the distal end 13b of the obturator is inserted into the proximal end of cannula 10 and the cannula slide 14 is pushed forward so that the obturator slides forward along the cannula 10 until the obturator slide is in front of the back end 12b of slot 12 in the cannula slide, at which position the lower segment 15 of the obturator slide can enter the slot 12 in the cannula slide. For removal, when the obturator slide 14 is at or near back end 12b of slot 12 in the cannula slide 11, the obturator slide 14 can be lifted out of this slot and pulled rearwardly past the back end of the cannula slide to slide the obturator out of the cannula 10 at the latter's proximal end.

Figure 1:
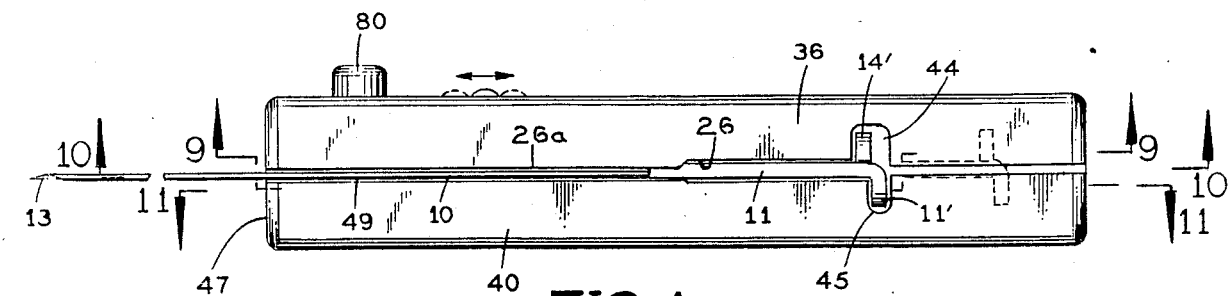
FIG. 1 is a top plan view of a spring-powered actuating mechanism holding the present biopsy needle.

As shown in FIG. 1, the spring-powered actuating mechanism 25 for the present biopsy needle has a housing with a narrow longitudinal recess 26 toward its back end for receiving and holding the cannula slide 11 and a narrower longitudinal recess 26a for receiving and holding the proximal part of the cannula 10. The housing has a front piece 47 with a narrow longitudal slot 49 that is a longitudinal extension of recess 26a. The cannula extends out of the housing at the front end of slot 49.

The housing of actuating mechanism 25 has an upper front wall 36 above recesses 26 and 26a and a lower front wall 40 below these recesses. The upper front wall 36 is formed with a slot 44 that opens into recess 26. Slot 44 receives the laterally projecting outer segment 14' of the obturator slide when the biopsy needle is inserted into the housing of actuating mechanism 25. The lower front wall 40 of this housing has a slot 45 that opens into recess 26 on the opposite side from slot 44 and is offset behind slot 44 lengthwise of the actuating mechanism by the same distance that the laterally projecting segment 11' of the cannula slide is offset behind the laterally projecting segment 14' of the obturator slide when they are positioned as shown in FIGS. 2 and 3. Slot 45 receives the laterally projecting segment 11' of the cannula slide when the biopsy needle is inserted into the housing of actuating mechanism 25.

Obviously, the biopsy needle is inserted into the housing of the actuating mechanism when the parts of the biopsy needle are positioned as shown in FIGS. 2 and 3. An incorrect insertion of the biopsy needle is not possible because of the longitudinal offset of the laterally projecting segments 11' and 14' of the cannula slide 11 and the obturator slide 14. That is, it is not possible to insert the biopsy needle into the housing of actuating mechanism 25 with the laterally projecting segment 11' of the cannula slide in slot 44 and the laterally projecting segment 14' of the obturator slide in slot 45.

Inside the housing of actuating mechanism 25, a first longitudinal channel or guideway 42 of rectangular cross-section (FIG. 14) is located on the side of longitudinal recesses 26 and 26a where slot 44 is located. This channel or guideway slidably receives an obturator slide bar 163 (FIGS. 10 and 14) which is substantially the same in its operation as the same-numbered part of the actuating mechanism disclosed in my aforementioned U.S. patent application Ser. No. 268,729. Slide bar 163 has a recess 165 (FIG. 12) which registers with slot 44 in the housing in one position of this slide bar longitudinally of the housing, so this recess can receive the laterally projecting segment 14' of the obturator slide to couple the obturator slide to slide bar 163. Thereafter, the slide bar 163 can be retracted (FIG. 10) to position its recess 165 behind and out of registration with slot 44 in the housing. Such retraction of the obturator slide bar 163 also retracts the obturator slide 14 and the obturator 13.

A second channel or guideway 43 (FIG. 14) of rectangular cross-section on the opposite side of longitudinal recesses 26 and 26a in the housing of actuating mechanism 25 slidably receives a cannula slide bar 63 (FIGS. 11 a 14) which corresponds to the same-numbered part of the actuating mechanism in application Ser. No. 268,729. Slot 45 intersects channel or guideway 43. Slide bar 63 has a recess 65 (FIG. 12) which registers with slot 45 in the housing in one position of this slide bar longitudinally of the housing, so this recess can receive the laterally projecting segment 11' of the cannula slide to couple the cannula slide to slide bar 63. Thereafter, the slide bar 63 can be retracted (FIG. 11) to position its recess 65 behind and out of registration with slot 45 in the housing. Such retraction of the cannula slide bar 63 also retracts the cannula slide 11 and the cannula 10.

The housing of the actuating mechanism 25 presents a flat, narrow, longitudinal shelf S between its channels 42 and 43. This shelf slidably supports the cannula slide 11 for movement between a forward-most position (FIG. 9) in which its lateral extension 11' registers with the housing slot 45 and its fully retracted position (FIGS. 10 and 11) in which its lateral extension 11' is spaced behind housing slot 45.

The actuating mechanism has a trigger button 80 (FIGS. 1 and 12-14) connected to a trigger slide 75 (FIG. 13) for selectively adjusting the position of the trigger slide transversely of the channels 42 and 43 between:

(1) a first position in which it holds both the cannula slide bar 63 and the obturator slide bar 163 retracted; and (2) an intermediate second position in which it holds the cannula slide bar 63 retracted and permits the obturator slide bar 163 to move to an extended position; and (3) a third position in which it permits the cannular slide bar 63 to move to an extended position.

In positions (1) and (3) of trigger slide 75, the cannula 10 covers the specimen-receiving recess 16 in the obturator, as shown in FIGS. 2 and 3. In position (2), the specimen-receiving recess 16 in the obturator is exposed beyond the distal end of the cannula, as shown in FIGS. 4 and 5.

The cannula slide bar 63 is powered by a spring 69 (FIG. 11) and the obturator slide bar 163 is powered by a spring 169 (FIG. 10) in the same manner as the same-numbered parts of the actuating mechanism in application Ser. No. 268,729.

The actuating mechanism herein also has a safety slide 85 (FIG. 14) having essentially the same construction and mode of operation as the same-numbered part of the actuating mechanism in application Ser. No. 268,729. This same slide determines how far in the trigger button 80 can be pushed. Safety slide 85 is selectively adjustable longitudinally of the housing of the actuating mechanism between three positions which determines the previously-mentioned three positions of trigger slide 75.

In the use of this actuating mechanism, after inserting the biopsy needle in the housing of the actuating mechanism, as shown in FIG. 1, the cannula slide bar 63 and the obturator slide bar 163 are simultaneously retracted by a cocking device (not shown herein) as shown at 110-116 in my U.S. patent application Ser. No. 268,729. This retracts the biopsy needle to the phantom line position in FIG. 1. FIG. 10 shows the obturator slide 163 and the biopsy needle in this retracted position. FIG. 11 shows the cannula slide 63 and the biopsy needle in this retracted position.

Then the safety slide 85 is moved forward to the position in which it prevents the trigger slide 75 from being pushed in so that it prevents both the cannula slide bar 63 and the obturator slide bar 163 from moving forward. Following this, the cocking device is removed from the actuating device 25. The distal end of the biopsy needle now is inserted into the patient to within about 1 cm. from where the tissue specimen is to be removed.

Next, the safety slide 85 is retracted to its half-way position. When the trigger button 80 now is pushed in, the trigger slide 75 moves in until it has released the cocked obturator slide bar 163, which is moved forward by its spring 169 to its extended position shown inside the housing of actuating mechanism 25. Recess 16 in obturator 13 now is exposed to the patient's body tissue, and the tissue specimen prolapses into this recess while the cannual slide bar 63 is held retracted by trigger slide 75.

After a time determined by the surgeon as sufficient for the tissue specimen to fully prolapse into the obturator recess 16, and if the surgeon now determines from the display screen of the ultrasonic scanner that this is where he wants the specimen taken, the surgeon fully retracts the safety slide 85 to the position in which it permits trigger button 80 to be pushed in all the way. Then the surgeon pushes the trigger button 80 in as far as it will go, so that the trigger slide 75 releases the cocked cannula slide bar 63, which under the impetus of spring 69 moves forward, causing the cannula 10 to move out along the obturator 13 to sever the tissue specimen that is in the obturator recess 16 from the adjoining body tissue and hold the captured tissue specimen in this recess.

Alternatively, instead of moving the safety slide 85 to its half-way position and thereafter to its fully retracted position, the safety slide 85 may be moved in one stroke from its fully disarmed position to its fully armed position. The surgeon can then move the trigger button 80 half-way in to release the obturator 13 and then all the way in to release the cannula 10 with the time interval between such movements controlled by the surgeon.

As another alternative, the surgeon can move the trigger button 80 all the way in using one stroke, producing rapid-fire sequential movements of the obturator 13 and then the cannula 10 where the time interval between them is determined by the speed at which the trigger slide 75 is pushed in. As already explained, in many surgical situations this would be less satisfactory because the surgeon does not control the time interval for the tissue specimen to prolapse into the obturator recess 16 before it is severed by the cannula 10.

The actuating device 25 may be removed from the biopsy needle after the sequential extensions of the obturator 13 and the cannula 10, as described, while the obturator and the cannula remain in the patient's body. Then the biopsy needle may be pulled out of the patient's body and the captured tissue specimen may be removed from the biopsy needle.

I claim:

1. A biopsy needle comprising:
   an elongated cannula having proximal and distal ends;
   a cannula slide attached to said proximal end of said cannula and having a laterally projecting segment which extends transversely on one side;
   an elongated obturator slidably extending longitudinally through said cannula and having proximal and distal ends, said obturator having a specimen-receiving recess near its distal end which is open along the outside of the obturator;
   and an obturator slide attached to said proximal end of said obturator and slidably engaging said cannula slide for selective adjustment of either slide along the other slide in a direction longitudinally of said cannula and obturator between a first position in which said cannula covers said specimen-receiving recess in said obturator and a second position in which said recess is exposed beyond said distal end of said cannula;
   said obturator slide having a laterally projecting segment which extends transversely on the opposite side from said projecting segment of said cannula slide and is offset longitudinally from said projecting segment of said cannula slide in all positions of said slides from said first position to said second position.

2. A biopsy needle according to claim 1 wherein said laterally projecting segment of said obturator slide is offset from said laterally projecting segment of said cannula slide toward said distal ends of said cannula and said obturator in all said positions of said slides.

3. A biopsy needle according to claim 1 wherein:
   said cannula slide extends from said proximal end of said cannula longitudinally in the opposite direction from said distal end of said cannula;
   said cannula slide has a slot therein which is elongated longitudinally, said slot having a front end toward said proximal end of said cannula and a back end away from said proximal end of said cannula;
   said obturator slide is slidably received in said slot;

and said obturator is flexible enough to permit said obturator slide to be removed from said slot near said back end of said slot for the slidable removal of said obturator from said cannula.

4. A biopsy needle according to claim 3 wherein:

said obturator slide engages said back end of said slot in said first position and said laterally projecting segment of said obturator slide is offset in front of said laterally projecting segment of said cannula slide in said first position.

5. A biopsy needle according to claim 1 wherein:

said cannula slide extends from said proximal end of said cannula longitudinally in the opposite direction from said distal end of said cannula;

said cannula slide has a slot therein which is elongated longitudinally, said slot having a front end toward said proximal end of said cannula and a back end away from said proximal end of said cannula;

said obturator slide is slidably received in said slot;

and said obturator slide engages said back end of said slot in said first position and said laterally projecting segment of said obturator slide is offset in front of said laterally projecting segment of said cannula slide in said first position.

* * * * *